United States Patent [19]

Cornils et al.

[11] 4,285,875

[45] Aug. 25, 1981

[54] PROCESS FOR PREPARING CARBOXYLIC ACIDS BY CATALYTIC OXIDATION OF ALDEHYDES

[75] Inventors: Boy Cornils; Werner De Win, both of Dinslaken; Jürgen Weber, Oberhausen, all of Fed. Rep. of Germany

[73] Assignee: Ruhrchemie Aktiengesellschaft, Oberhausen, Fed. Rep. of Germany

[21] Appl. No.: 172,620

[22] Filed: Jul. 28, 1980

[30] Foreign Application Priority Data

Aug. 1, 1979 [DE] Fed. Rep. of Germany ....... 2931154

[51] Int. Cl.³ .............................................. C07C 53/00
[52] U.S. Cl. .................................... 260/413; 562/418; 562/531; 562/536; 252/438
[58] Field of Search ................ 260/406, 413 N, 413 J, 260/413 R; 562/531, 536, 418; 252/438

[56] References Cited

U.S. PATENT DOCUMENTS

| | | | |
|---|---|---|---|
| 1,937,528 | 12/1933 | Oxley et al. | 562/536 |
| 2,010,358 | 8/1935 | Groll et al. | 562/531 |
| 3,816,522 | 6/1974 | Goldstein | 562/418 |

FOREIGN PATENT DOCUMENTS 1161972  8/1969  United Kingdom ..................... 562/531

*Primary Examiner*—John F. Niebling
*Attorney, Agent, or Firm*—Bierman & Bierman

[57] ABSTRACT

A process for preparing carboxylic acids by the oxidative conversion of the corresponding aldehydes comprises oxidizing the aldehydes in the presence of a catalyst comprising the anion $[Fe(CN)_5H_2O]^{-3}$. The catalyst may be selected from $[Fe(CN)_5H_2O]^{-3}$, compounds that form $[Fe(CN)_5H_2O]^{-3}$ under the reaction conditions, and their salts. The catalyst is useful for the oxidation of aldehydes with oxygen or oxygen-containing gases. The present process permits the use of lower reaction times and temperatures, and reduces the formation of undesirable reaction by-products.

17 Claims, No Drawings

PROCESS FOR PREPARING CARBOXYLIC ACIDS BY CATALYTIC OXIDATION OF ALDEHYDES

This application claims the priority of German Application No. P 29 31 154.4 filed Aug. 1, 1979.

The present invention is directed to a process for preparing carboxylic acids from aldehydes by oxidation with oxygen or oxygen-containing gases.

The preparation of carboxylic acids has been preferably conducted with the corresponding aldehydes, on account of the smooth and easy oxidative conversion of the aldehyde group into the carboxyl group. These reactions have primarily used oxygen, either in the pure form or mixed with inert gases as the oxidizing agent. The oxidation reaction may be conducted either with or without catalysts, and preferably proceeds at the lowest possible temperature in order to avoid secondary reactions causing formation of undesired by-products. In the instance where the reaction is catalyzed, the catalysts mainly used have been salts of transition metals, in particular salts of cobalt, manganese, chromium, iron, copper, nickel, silver and vanadium.

The reaction of aldehydes to convert them to carboxylic acids is frequently accompanied by secondary reactions and decomposition reactions, regardless of whether the conversion reaction is carried out in the presence of catalysts. In such cases, it is known to add alkali metal salts of weak acids to the reaction mixture to improve the selectivity of the oxidation of the aldehydes to the corresponding carboxylic acids. The disadvantage of this procedure, however, is that the added salts have an inhibiting effect on the reaction, with the result that the reaction time must be extended to attain the complete conversion of the starting substance.

In view of the above, an object of the invention is to develop a process for the oxidative conversion of aldehydes to carboxylic acids that provides a selective conversion of the aldehyde in the shortest possible reaction time.

The present invention comprises a process for preparing carboxylic acids by the catalytic oxidation of the corresponding aldehydes with oxygen or oxygen-containing gases, in the presence of a catalyst comprising the anion $[Fe(CN)_5H_2O]^{-3}$. In particular, the catalyst is selected from the group consisting of $[Fe(CN)_5H_2O]^{-3}$, compounds that form $[Fe(CN)_5H_2O]^{-3}$ under the reaction conditions, and salts thereof.

The present process is useful for the conversion of a variety of aldehydes to carboxylic acids having the same number of carbon atoms. Thus, the process may be employed with both straight and branched-chain aldehydes which may be selected from aliphatic aldehydes, cycloaliphatic aldehydes, araliphatic aldehydes and aromatic aldehydes. Preferably, aldehydes as defined above having from 4 to 10 carbon atoms are converted by this process; examples of suitable aldehydes are acetaldehyde, propionaldehyde, butyraldehyde, valeraldehyde, heptanal, cycloaliphatic aldehydes such as formylcyclohexane; araliphatic aldehydes such as phenylpropanal; and aromatic aldehydes such as benzaldehyde. The present process is particularly useful with branched aldehydes, and specifically α-branched aldehydes, as the latter have been found to decompose to formic acid and formic acid esters when they are subjected to know oxidation processes.

The catalyst employed in the present process is an anionic complex having the formula $[Fe(CN)_5H_2O]^{-3}$, and includes compounds and salts providing this complex anion to the reaction mixture. The preparation of compounds containing the complex anion is known. For example, the sodium salt, $Na_3[Fe(CN)_5H_2O]$ may be prepared from $Na_3[Fe(CN)_5NH_3]$ by reaction with sodium hydroxide. Also, as disclosed in an article by Jimori, in Z. Anorg. Chem. 167,145 (1927), hexacyano compounds of iron can be converted into compounds containing the pentacyano-aquo anion utilized herein. Further, complex iron compounds containing 5 cyanide groups, referred to as "prusside" compounds, may be added directly to the aldehyde reaction mixture, and will form the desired anion under the reaction conditions of the oxidative conversion. Examples of such complex compounds are those containing the anion $[Fe(CN)_5Z]^{-3}$, where Z may be ammonia or aromatic nitrogen heterocyclic compounds. A particular compound is sodium-iron (II)-ammine-pentacyanide-trihydrate.

In practice, the complex anion catalyst is added to the aldehyde in an amount of at least 0.05% by weight of the aldehyde. Depending upon the nature of the aldehyde, the catalyst may be only partially soluble in the reaction medium, and may also exist as a heterogeneous phase if added in comparatively large amounts. In a preferred embodiment, the catalyst may be added in amounts of from 0.1 to 2% by weight of the aldehyde. Applicants have found presence of the undissolved catalyst at the upper limits of this range exerts a positive effect on the oxidative conversion of the aldehydes.

The process is carried out at temperatures ranging up to about 50° C., and preferably from 20° to 50° C. The employment of higher reaction temperatures is undesirable, as the catalyst tends to be thermally unstable, and the decomposition products of the reaction exhibit little activity.

The reaction time of the present process depends upon the reaction temperature employed, and may, in the instance of isobutryaldehyde, range from 0.5 to 6 hours; thus, at 30° C., the oxidation of isobutryaldehyde goes to completion after about 2 hours.

The process is practiced by first combining the aldehyde reactant with the catalyst. Thus, the catalyst may be dissolved in the aldehyde, and, as mentioned earlier, partially suspended therein. The use of a solvent to prepare the reaction mixture is not absolutely necessary, but may be desirable and even recommended in certain cases. For example, in the instance where unstable aldehydes, such as hydroxyaldehydes are being reacted, it is advisable to utilize a solvent. For example, suitable solvents may include, without limitation, aliphatic hydrocarbons, aromatic hydrocarbons, aliphatic carboxylic acids and aromatic carboxylic acids.

The reaction mixture prepared above is then placed in a suitable reactor, such as a tubular reactor into which the reactants flow from the bottom. The reaction proceeds by passing the oxygen or oxygen-containing gas mixture through the bottom entrance of the reactor, and thence through the reaction mixture. The amount of oxidizing agent may vary, and an excess of oxidizing agent is not harmful, particularly if the reaction is carried out at a lower temperature range.

The process of the present invention is an improvement over the known oxidative conversions, as the reaction time and the proportion of undesired by-products formed are both reduced.

The present invention is illustrated in the following examples.

EXAMPLE 1

This example was prepared as a comparative illustration of conventional oxidative conversion of aldehydes. Thus, 202 grams (2.8 mole) of isobutyraldehyde was placed in a 1 liter volume double jacket reaction tube provided with a glass frit, and oxygen was added thereto. During the reaction which followed, the temperature of the mixture was maintained constant at 30° C. The degree of conversion of the aldehyde to the acid was determined by monitoring the neutralization number of the reaction mixture. After 5 hours, a neutralization number of 588 was reached, and the reaction was considered completed. The total amount of by-products formed was found to be 4.2% by weight of the total mixture of reaction products.

EXAMPLE 2

In this example, the oxidative conversion of isobutyraldehyde was conducted under similar conditions to those set forth in Example 1, with the exception that 4.5 mmole of the catalyst tripotassium-aquo-pentacyanoferrate (II), corresponding to about 0.92 grams of $[Fe(CN)_5H_2O]^{-3}$ was initially added to the aldehyde. The reaction proceeded at the same temperature, and after about 3 hours, the neutralization number of the reaction mixture reached the value stated in Example 1, indicating that the like degree of conversion of the aldehyde had occurred. The total amount of by-products found in this reaction mixture was only 2.8% by weight.

EXAMPLE 3

In similar manner to Example 2, a second oxidative conversion of isobutyraldehyde was conducted under similar conditions to that of Example 1, with the exception, however, that 6.2 mmole of the catalyst sodium-iron (II)-ammine-pentacyanide-trihydrate was added as a $[Fe(CN)_5H_2O]^{-3}$-forming substance, corresponding to approximately 1.3 grams of $[Fe(CN)_5H_2O]^{-3}$. This reaction reached the neutralization number given in Example 1 after about 2 hours. The total quantity of by-products formed was only 1.7% by weight.

EXAMPLES 4–9

In these examples, the process was conducted in accordance with the procedures described in Examples 1–3 above. Examples 4, 6 and 8 comprise reactions wherein no catalyst was present, while Examples 5, 7 and 9 included the presence of the catalyst sodium-iron (II)-ammine-pentacyanide-trihydrate as a $[Fe(CN)_5H_2O]^{-3}$-forming substance. The reaction parameters, including the amount of catalyst, reaction temperatures and times, neutralization numbers and percent of by-products formed are set forth in the following table.

TABLE

| Example | 4 | 5 | 6 | 7 | 8 | 9 |
|---|---|---|---|---|---|---|
| Aldehyde | n-Valeraldehyde | | 2-Ethylhexanal | | 2-Ethylbutanal | |
| Amount of aldehyde (moles) | 2.3 | | 1.6 | | 2.0 | |
| Amount of catalyst (mmoles) | None | 6.1 | None | 6.3 | None | 6.1 |
| Reaction temperature (°C.) | 30 | 30 | 40 | 40 | 40 | 40 |
| Neutralization number | 516 | 516 | 305 | 333 | 384 | 412 |
| Reaction time (hrs) | 6.5 | 3 | 7 | 4 | 6 | 3 |
| Total amount of by-products (% by weight) | 3.1 | 0.6 | 23.5 | 15.3 | 20.5 | 15.4 |

What we claim is:

1. A process for preparing carboxylic acids comprising reacting the corresponding aldehyde in the presence of a catalyst comprising the anion $[Fe(CN)_5H_2O]^{-3}$.

2. The process of claim 1 wherein said aldehydes are selected from straight chain and branched-chain aldehydes.

3. The process of claim 1 wherein said straight chain and branched-chain aldehydes are selected from aliphatic aldehydes, cycloaliphatic aldehydes, araliphatic aldehydes and aromatic aldehydes.

4. The process of claim 2 wherein said aldehydes have from 4 to 10 carbon atoms.

5. The process of claim 2 wherein said aldehydes are α-branched-chain aliphatic aldehydes.

6. The process of claim 1 wherein said catalyst is selected from $[Fe(CN)_5H_2O]^{-3}$, compounds that form $[Fe(CN)_5H_2O]^{-3}$ under the reaction conditions, and salts thereof.

7. The process of claim 6 wherein said catalyst comprises $Na_3[Fe(CN)_5H_2O]$.

8. The process of claim 6 wherein the compound that forms $[Fe(CN)_5H_2O]^{-3}$ under the reaction conditions is sodium-iron (II)-ammine-pentacyanide-trihydrate.

9. The process of claim 1 wherein said catalyst is present in an amount of at least 0.05% by weight of said aldehyde.

10. The process of claim 9 wherein said catalyst is present in an amount of from 0.1% to 2% by weight of said aldehyde.

11. The process of claim 1 wherein said aldehyde is reacted at a temperature up to about 50° C.

12. The process of claim 11 wherein said aldehyde is reacted at a temperature up to 20° C. to about 50° C.

13. The process of claim 1 wherein said aldehyde is reacted for a period of time of up to about 6 hours.

14. The process of claim 1 wherein prior to reacting said aldehyde, said catalyst is at least partially dissolved therein.

15. The process of claim 14 further including the presence of a solvent.

16. The process of claim 15 wherein said solvent is selected from aliphatic hydrocarbons, aromatic hydrocarbons, aliphatic carboxylic acids and aromatic carboxylic acids.

17. The process of claim 1 wherein said aldehyde is oxidized by contact with a source of oxygen selected from gaseous $O_2$ and an oxygen-containing gas mixture.

* * * * *